United States Patent
Park (10) Patent No.: US 12,263,272 B2
(45) Date of Patent: *Apr. 1, 2025

(54) BONE GRAFT COMPOSITION AND MANUFACTURING METHOD THEREOF

(71) Applicant: MedPark Co., Ltd, Busan (KR)

(72) Inventor: JungBok Park, Busan (KR)

(73) Assignee: MedPark Co., Ltd, Busan (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/927,845

(22) Filed: Jul. 13, 2020

(65) Prior Publication Data

US 2021/0299327 A1 Sep. 30, 2021

(30) Foreign Application Priority Data

Mar. 31, 2020 (KR) .................. 10-2020-0039212

(51) Int. Cl.
*A61L 27/26* (2006.01)
*A61L 27/56* (2006.01)

(52) U.S. Cl.
CPC ............. *A61L 27/26* (2013.01); *A61L 27/56* (2013.01); *A61L 2430/02* (2013.01)

(58) Field of Classification Search
CPC ...... A61L 27/26; A61L 27/34; A61L 27/3608; A61L 27/365
See application file for complete search history.

(56) References Cited

U.S. PATENT DOCUMENTS

| | | | | |
|---|---|---|---|---|
| 5,824,084 A | * | 10/1998 | Muschler | ............... A61L 27/32 |
| | | | | 128/898 |
| 2008/0031917 A1 | | 2/2008 | Miller et al. | |
| 2012/0205274 A1 | * | 8/2012 | Sunwoo | ............ A61L 27/3608 |
| | | | | 424/549 |
| 2013/0189338 A1 | | 7/2013 | Drapeau et al. | |
| 2016/0279287 A1 | * | 9/2016 | Bachert | ............... A61L 24/0094 |
| 2018/0000987 A1 | | 1/2018 | Yang et al. | |

FOREIGN PATENT DOCUMENTS

| | | | |
|---|---|---|---|
| CN | 105228660 A | 1/2016 | |
| CN | 110755686 A | * 2/2020 | ............ A61L 27/20 |
| EP | 2 978 463 A1 | 2/2016 | |
| EP | 3 323 437 A1 | 5/2018 | |
| JP | 04-361757 A | 12/1992 | |
| KR | 10-2002-0014034 A | 2/2002 | |
| KR | 10-1030429 B1 | 4/2011 | |

(Continued)

OTHER PUBLICATIONS

Machine translation of CN-110755686-A. (Year: 2020).*

(Continued)

*Primary Examiner* — Carlos A Azpuru
*Assistant Examiner* — Casey S Hagopian
(74) *Attorney, Agent, or Firm* — Lathrop GPM LLP; Brian C. Trinque (57) ABSTRACT

The present disclosure relates to a bone graft composition, and more particularly, to a bone graft composition containing hydroxypropyl methylcellulose and a preparation method therefor. In addition, the present disclosure relates to a bone graft composition containing hydroxypropyl methylcellulose in an amount that provides shape retainability, and a preparation method therefor.

20 Claims, 2 Drawing Sheets

(56) References Cited

FOREIGN PATENT DOCUMENTS

| | | |
|---|---|---|
| KR | 10-2012-0097521 A | 9/2012 |
| KR | 10-1443814 B1 | 9/2014 |
| KR | 10-2015-0006507 A | 1/2015 |
| KR | 10-2017-0015802 A | 2/2017 |
| KR | 10-1962251 B1 | 5/2017 |
| KR | 10-1779377 B1 | 9/2017 |
| KR | 10-2066392 B1 | 5/2019 |
| WO | WO-2016032197 A1 * | 3/2016 ............... A61F 2/28 |

OTHER PUBLICATIONS

Machine translation of WO-2016032197-A1. (Year: 2016).*
Decision to grant a patent mailed Nov. 30, 2020 from Korean Industrial Property Office for Korean Patent Application No. 10-2020-0039212 and its English translation.
Notice of Preliminary Rejection mailed Jun. 24, 2020 from Korean Industrial Property Office for Korean Patent Application No. 10-2020-0039212 and its English translation.
European Search Report for EP Application No. EP 20184783 dated Dec. 14, 2020, 2 pages.

* cited by examiner

FIG. 1

Step of preparing bone morphogenetic protein solution

⇩

Step of adsorbing bone morphogenetic protein onto graft material powder

⇩

Step of forming gel after mixing hydroxypropyl methylcellulose powder

⇩

Step of forming porous sponge-like structure

⇩

Step of sterilizing bone graft composition

FIG. 2

BONE GRAFT COMPOSITION AND MANUFACTURING METHOD THEREOF

CROSS-REFERENCE TO RELATED APPLICATION(S)

This application claims priority to Korean Patent Application No. 10-2020-0039212, filed on Mar. 31, 2020, the disclosure of which is incorporated herein by reference in its entirety.

BACKGROUND OF THE DISCLOSURE

Technical Field

The present disclosure relates to a bone graft composition having excellent shape retainability and a preparation method therefor.

Description of the Related Art

Various materials and various methods may be used for reconstruction of defective bone. For example, bone graft materials such as bone powders, bone chips, and bone blocks may be used, or methods such as autografting, allografting, and xerografting may be used for reconstruction of defective bone.

Bone graft materials that are used for reconstruction of defective bone may be used in orthopedic surgery, neurosurgery, plastic surgery, otolaryngology, Oral and Maxillofacial Surgery, Department of Veterinary Medicine (veterinary clinic), dermatology and dentistry. For example, these materials may be used for bone defects during disc surgery to induce bone regeneration, or may also be used for implant surgery and reconstruction of oral and maxillofacial bone defects.

Meanwhile, Korean Patent No. 10-0401941 discloses technology related to a bone graft material and a preparation method therefor. When a reticular bone is used which is composed of bioceramic powder and has a three-dimensionally communicating pore structure as disclosed therein, there may be limitations in the effect of bone graft in terms of biocompatibility, mechanical properties, toxicity, and the like.

SUMMARY

An object of the present disclosure is to provide a bone graft composition containing hydroxypropyl methylcellulose, which has excellent shape retainability, and a preparation method therefor.

One embodiment of the present disclosure provides a bone graft composition having shape retainability of 50 or more, wherein the shape retainability is defined as a value obtained by dividing a maximum breaking force (Nmax) by a short-axis change rate, in which the maximum breaking force is a force at which a change in the shape of a sphere-shaped material occurs, and the short-axis change rate is the ratio of the reduction in short-axis length of the sphere-shaped material, measured after the change in the shape occurred, to the diameter of the sphere-shaped material.

The bone graft composition contains 1 part by weight of a bone graft material mixed with 0.3 to 3 parts by weight of hydroxypropyl methylcellulose.

One embodiment of the present disclosure provides a bone graft composition having excellent shape retainability, wherein the porous bone graft material is a natural bone graft material.

One embodiment of the present disclosure provides a method for preparing a bone graft composition having excellent shape retainability, the method including steps of:
(1) preparing a bone morphogenetic protein solution by mixing a solvent and a bone morphogenetic protein; (2) adsorbing the bone morphogenetic protein onto graft material powder by mixing the bone morphogenetic protein and the graft material powder; (3) mixing and stirring the graft material powder having the bone morphogenetic protein adsorbed thereon and hydroxypropyl methylcellulose powder to form a gel that imparts shape retainability to the bone graft composition; and (4) forming a structure containing a plurality of pores by freeze-drying the gel under vacuum.

One embodiment of the present disclosure provides a method for preparing a bone graft composition having excellent shape retainability, wherein the bone morphogenetic protein is at least one selected from the group consisting of BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, BMP-18, recombinant bone morphogenetic proteins thereof, and bone morphogenetic proteins equivalent thereto.

One embodiment of the present disclosure provides a method for preparing a bone graft composition having excellent shape retainability, wherein the concentration of the bone morphogenetic protein in the bone morphogenetic protein solution may be 0.05 to 0.15 mg/ml.

One embodiment of the present disclosure provides a method for preparing a bone graft composition having excellent shape retainability, wherein the pH of the bone morphogenetic protein solution is adjusted to 4.6 to 5 using phosphate buffer saline.

One embodiment of the present disclosure provides a method for preparing a bone graft composition having excellent shape retainability, wherein the volume ratio between the graft material powder having the bone morphogenetic protein adsorbed thereon and the hydroxypropyl methylcellulose powder in step (3) is 1:0.2 to 1:0.6.

One embodiment of the present disclosure provides a method for preparing a bone graft composition having excellent shape retainability, wherein the method further includes a step of sterilizing the bone graft composition by ethylene oxide gas or gamma-ray irradiation.

One embodiment of the present disclosure provides a method for preparing a bone graft composition having excellent shape retainability, wherein the concentration of the ethylene oxide gas is 450 to 1200 mg/l, or the dose of the gamma-ray irradiation is 10 to 25 kGy.

DESCRIPTION OF SPECIFIC EMBODIMENTS

Embodiments of the present disclosure relate to a bone graft composition which may have excellent effects in terms of activation of bone formation, biocompatibility, and ease of use by containing a porous bone graft material and hydroxypropyl methylcellulose.

However, description of a portion of a particular embodiment, which overlaps with that of other embodiments, will be omitted for a clearer and more concise explanation. Even though description of that portion is omitted, the portion is not excluded from the present disclosure and the scope of rights thereof should be admitted in the same manner as that of other embodiments.

In the following description, the detailed description of publicly-known technology related to the present disclosure will be omitted when it may unnecessarily obscure the subject matter of the present disclosure. In addition, the terms used in the following description are terms defined in consideration of their functions in the present disclosure and may be changed according to the intention of a user or an operator, or according to practice. Therefore, the definitions of these terms should be determined based on the contents throughout the specification.

The technical spirit of the present disclosure is determined by the claims, and the following embodiments are merely means for efficiently explaining the technical spirit of the present disclosure to those skilled in the art to which the present disclosure pertains.

In the present disclosure, when the repeating unit, compound or resin represented by a formula includes isomers thereof, the corresponding formula representing the repeating unit, compound or resin means a representative formula that also represents the isomers.

Hereinafter, specific embodiments of the present disclosure will be described. However, these embodiments are only examples, and the present disclosure is not limited thereto.

The bone graft composition may be implanted into a bone defect, and may be used to restore the bone defect by filling the bone defect. Hereinafter, 'implant' includes being applied into a bone defect in the state of not having rigidity or in the state of having rigidity. Applying into a bone defect in the state of having rigidity may being implanted into a bone defect after being formed the shape corresponding to the shape of the bone defect in the state of having rigidity by a shape forming device, for example 3 dimensional printer.

A bone graft composition of the present disclosure contains a porous bone graft material and hydroxypropyl methylcellulose. The bone graft composition may be implanted into a bone defect, and may be used to restore the bone defect by filling the bone defect.

The bone graft material may be natural bone. For example, it may be autogenous bone, allogeneic bone, or xenogenic bone. When the natural bone is used, it may exhibit an excellent bone formation effect, because it has excellent biocompatibility and also has good wettability and hygroscopicity due to a large number of pores contained therein. In addition, the natural bone may also be used for reconstruction of defective bone in orthopedic surgery, neurosurgery, plastic surgery, otolaryngology, Oral and Maxillofacial Surgery, Department of Veterinary Medicine (veterinary clinic), dermatology and dentistry.

In addition, the bone graft material may also be used for reconstruction of defective bone in human or animals. Hereinafter, it mainly described the usage to the dentistry, however, the usage does not limited thereto.

As the bone graft composition contains hydroxypropyl methylcellulose, the bone graft composition may have adhesion to a bone defect. At the same time, shape retainability may be imparted to the bone graft composition by the HPMC. When the bone graft composition has excellent shape retainability, even if the bone graft composition is applied to the maxilla, it may be applied to fit the bone defect without flowing down, and thus even if there is an impact due to mastication motion or the like, the bone graft composition may be prevented from being detached from the bone defect, and at the same time, the medical procedure can be more easily performed.

Figure 2:
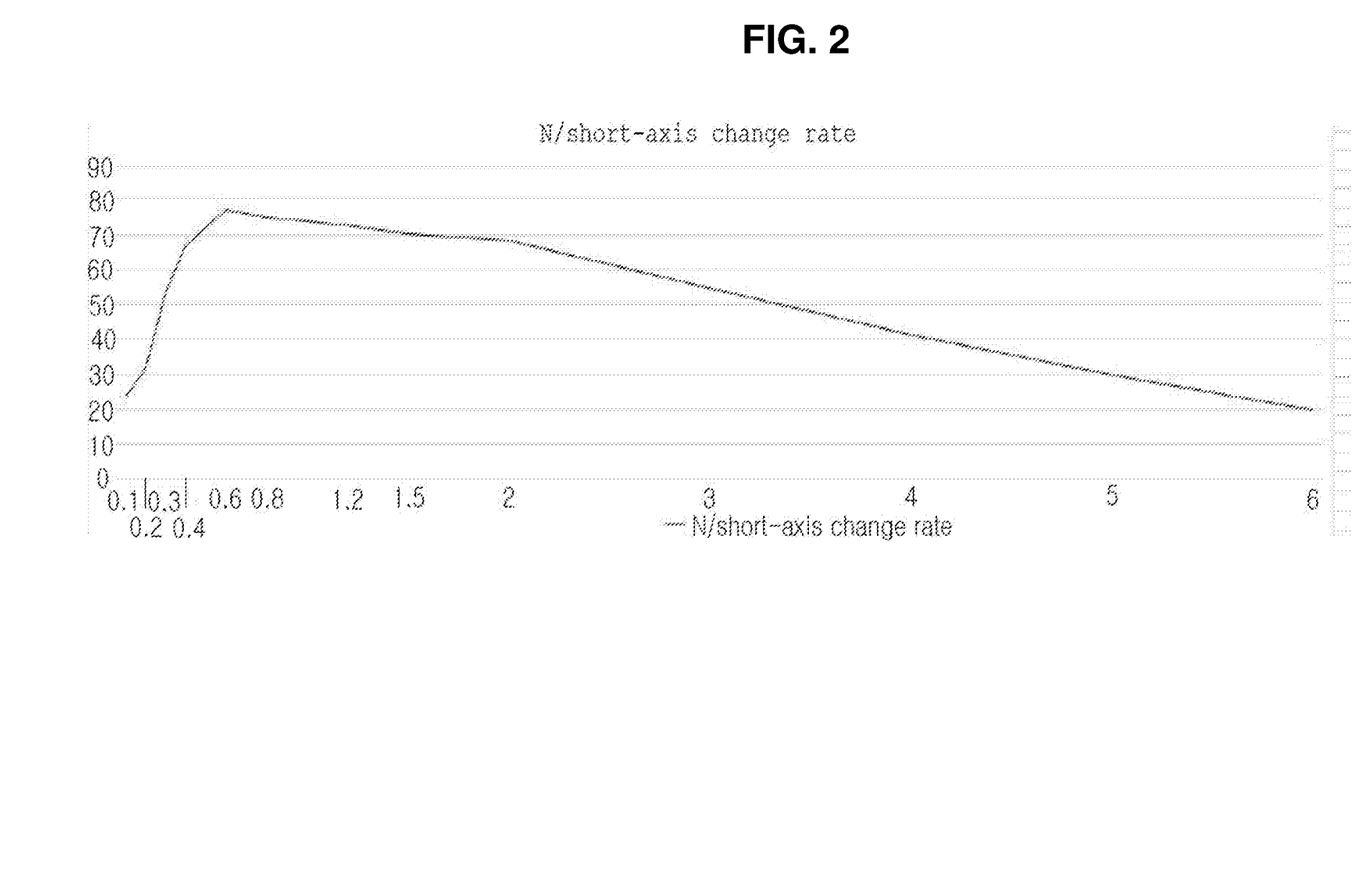
FIG. 2 shows "maximum breaking force (N) of bone graft composition sphere/short-axis change rate of bone graft composition sphere" as a function of the content (parts by weight) of hydroxypropyl methylcellulose, and demonstrates the content (parts by weight) of hydroxypropyl methylcellulose for a bone graft composition having excellent shape retainability.

In order to ensure shape retainability, the bone graft composition according to one embodiment of the present disclosure may contain hydroxypropyl methylcellulose in an amount of 0.3 to 3 parts by weight, more preferably 0.4 to 2 parts by weight, based on 1 part by weight of the porous bone graft material. In this case, the shape retentability of the composition is further enhanced. As can be seen from the Experimental Example to be described later, it was confirmed that, as the content of the hydroxypropyl methylcellulose increased, the short-axis change rate increased, and the maximum breaking force tended to increase and then decrease. As shown in FIG. 2, it can be seen that this increase or decrease was rapid. Through this, it was confirmed that a bone graft composition having shape retainability can be provided when the content of the hydroxypropyl methylcellulose is 0.3 to 3 parts by weight based on 1 part by weight of the bone graft material. If the content of the hydroxypropyl methylcellulose is less than 0.3 parts by weight based on 1 part by weight of the bone graft material, the effect of adding the hydroxypropyl methylcellulose (HPMC) may be insignificant due to an excessively low content of the hydroxypropyl methylcellulose (HPMC), and thus the bone graft material can be easily pressed and broken even by low pressure (force) so that the shape of the bone graft material cannot be suitably retained. On the other hand, if the content of the hydroxypropyl methylcellulose is more than 3 parts by weight based on 1 part by weight of the porous bone graft material, the bone graft material can be easily pressed even by a small force due to an excessively high content of the hydroxypropyl methylcellulose (HPMC) and even the short-axis change rate can increase so that the shape of the bone graft material cannot be suitably retained.

A bone graft composition kit according to another embodiment of the present disclosure includes the above-described bone graft composition and a syringe containing the composition. By providing the syringe directly containing the bone graft composition, it is possible to ensure ease of use and significantly reduce the possibility of contamination that may occur during use.

However, in the description of this embodiment, the description of a portion that overlaps with that of the above-described embodiments is omitted for a clearer and more concise explanation. Even though the description of that portion is omitted, the portion is not excluded from the present disclosure and the scope of rights thereof should be admitted in the same manner as that of the above-described embodiment.

A method for preparing a bone graft composition according to still another embodiment of the present disclosure includes steps of: preparing a bone morphogenetic protein solution by adding a bone morphogenetic protein to a solvent or adding the bone morphogenetic protein to the solvent and dissolving the bone morphogenetic protein in the solvent;

mixing and stirring graft material powder having the bone morphogenetic protein adsorbed thereon and hydroxypropyl methylcellulose powder to form a viscous gel that imparts shape retainability to the bone graft composition; and forming a sponge-like structure containing a plurality of pores by freeze-drying the mixture of the graft material powder and the hydroxypropyl methylcellulose powder, obtained by the mixing and stirring process, at low temperature under vacuum. The bone graft composition prepared through these steps may have excellent effects in terms of activation of bone formation, biocompatibility, and ease of use.

However, in the description of this embodiment, the description of a portion that overlaps with that of the above-described embodiments is omitted for a clearer and more concise explanation. Even though the description of that portion is omitted, the portion is not excluded from the present disclosure and the scope of rights thereof should be admitted in the same manner as that of the above-described embodiments.

Figure 1:
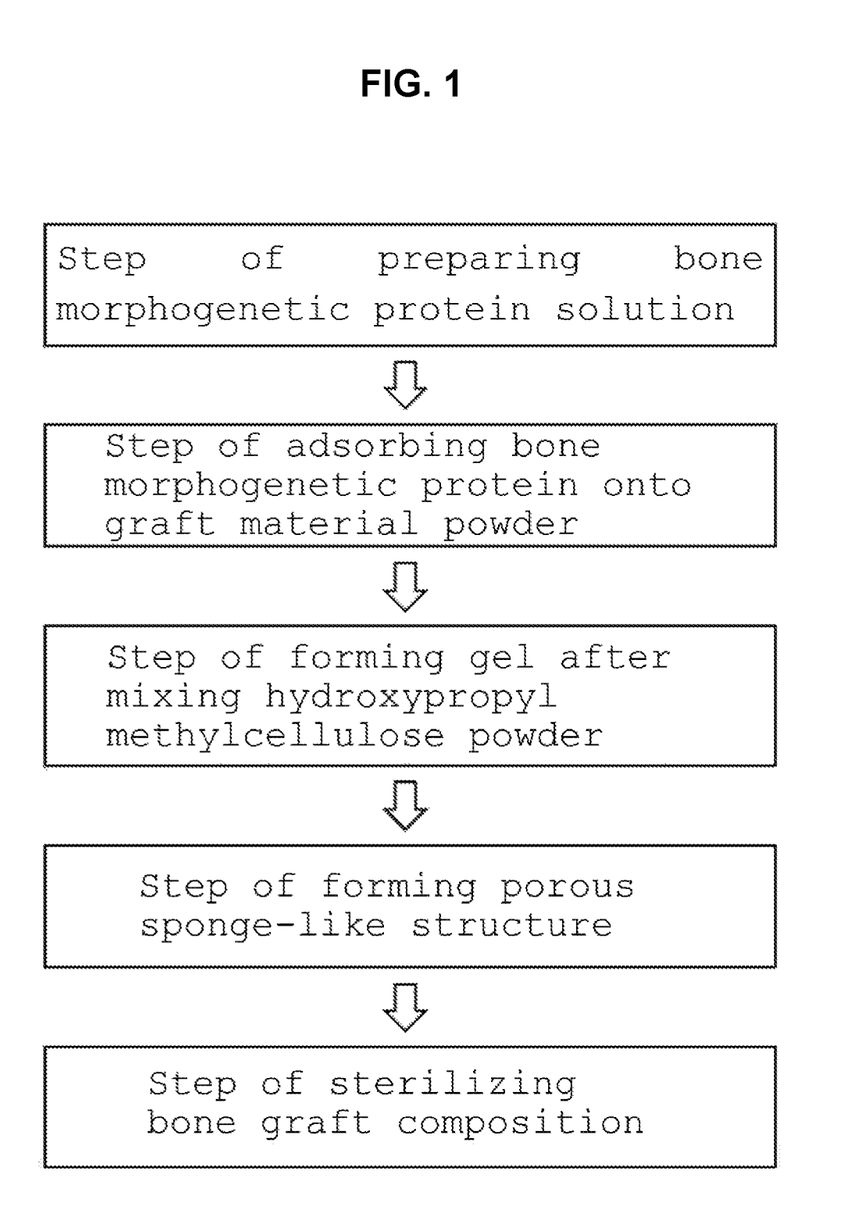
FIG. 1 is a flow diagram schematically showing a method for preparing a bone graft composition according to one embodiment of the present disclosure.

FIG. 1 is a flow diagram schematically showing a method for preparing a bone graft composition according to one embodiment of the present disclosure.

FIG. 2 shows "maximum breaking force (N) of bone graft composition sphere/short-axis change rate of bone graft composition sphere" as a function of the content (parts by weight) of hydroxypropyl methylcellulose, and demonstrates the content (parts by weight) of hydroxypropyl methylcellulose for a bone graft composition having excellent shape retainability.

First, a bone morphogenetic protein solution is prepared by dissolving a bone morphogenetic protein in a solvent. The bone morphogenetic protein solution may be prepared by adding the bone morphogenetic protein to the solvent, or adding the bone morphogenetic protein to the solvent and dissolving the bone morphogenetic protein in the solvent.

The bone morphogenetic protein may be at least one selected from the group consisting of BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, BMP-18, recombinant bone morphogenetic proteins thereof, and bone morphogenetic proteins equivalent thereto. Preferably, the bone morphogenetic protein may be rhBMP-2 in terms of the bone formation effect of the present disclosure.

According to one embodiment of the present disclosure, the concentration of the bone morphogenetic protein in the bone morphogenetic protein solution may be 0.05 to 0.15 mg/ml, preferably 0.08 to 0.12 mg/ml. When the concentration of the bone morphogenetic protein is within the above-described range, bone formation by the bone morphogenetic protein may be activated. If the concentration of the bone morphogenetic protein is less than 0.05 mg/ml, the ability of the bone morphogenetic protein to form new bone may be reduced, and if the concentration of the bone morphogenetic protein is more than 0.15 mg/ml, it may cause adverse effects.

In addition, according to one embodiment of the present disclosure, the pH of the bone morphogenetic protein solution may be, for example, 4.6 to 5. When the pH is within the above-described range, bone formation by the bone morphogenetic protein may be activated. If the pH of the bone morphogenetic protein solution is less than 4.6, the ability to form new bone may be reduced, and if the pH of the bone morphogenetic protein solution is more than 5, the ability to form new bone may be reduced. For example, the pH may be adjusted using phosphate buffer saline. When the pH is adjusted using phosphate buffer saline, the composition may have the effect of forming new bone.

Thereafter, the bone morphogenetic protein is adsorbed onto graft material powder by soaking the graft material powder with the bone morphogenetic protein solution. The previously prepared graft material powder may be soaked with the bone morphogenetic protein solution by flushing the graft material powder with the bone morphogenetic protein solution or dropping the graft material powder into the bone morphogenetic protein solution, whereby the bone morphogenetic protein may be adsorbed onto the graft material powder.

The graft material powder may be autogenous bone, allogeneic bone, or xenogenic bone. For example, the graft material powder may be prepared by placing it in a snap tube.

The average particle diameter (D50) of the graft material powder may be 200 to 5,000 μm, preferably 250 to 1,000 μm. If the average particle diameter of the powder is less than 200 μm, the graft material may be absorbed rapidly, and thus osteoconduction required for bone formation may be insufficient, and if the average particle diameter of the powder is more than 5,000 μm, precise processing of the graft material powder during application to a patient may be difficult.

According to one embodiment of the present disclosure, the step of adsorbing the bone morphogenetic protein onto the graft material powder may include a step of adsorbing the bone morphogenetic protein using a refrigerated centrifuge.

In some cases, the bone morphogenetic protein may also be suspended in the solution. However, when the bone morphogenetic protein is adsorbed while it is rotated at high speed using a centrifuge, the bone morphogenetic protein can be prevented from being suspended in the solution, and thus the bone morphogenetic protein may be easily adsorbed onto the surface or into the pores of the graft material powder. Only when the bone morphogenetic protein is adsorbed while it is rotated at high speed, it can be prevented from being suspended again after detachment from the graft material powder. If the bone morphogenetic protein is rotated at low speed, it can be suspended, and hence cannot be easily adsorbed. Under high-speed rotation, the bone morphogenetic protein can be adsorbed quickly onto the surface or into the pores of the graft material powder.

According to one embodiment of the present disclosure, the rotational speed of the refrigerated centrifuge may be 4,000 rpm or more. When the bone morphogenetic protein is adsorbed using the centrifuge, the higher the rotational speed, the better the adsorption. For example, the rotational speed of the centrifuge may be 4,000 rpm or more, and when this rotational speed range is satisfied, the bone morphogenetic protein can be prevented from being suspended in the solution.

According to one embodiment of the present disclosure, the step of adsorbing the bone morphogenetic protein using the refrigerated centrifuge may be performed at a cold temperature of 5° C. or below. As the step of adsorbing the bone morphogenetic protein using the refrigerated centrifuge is performed at a cold temperature of 5° C. or below, it is possible to maximize the effect of adsorbing the bone morphogenetic protein onto the surface or into the pores of the graft material powder through rotation while preventing the denaturation of the bone morphogenetic protein that is weak to heat, by preventing the temperature of the solution from being increased due to rotation. The cold temperature may be a temperature at which the solution does not freeze. For example, the cold temperature may be 5° C. or below, preferably 0.5 to 1.5° C.

Thereafter, the graft material powder having the bone morphogenetic protein adsorbed thereon and hydroxypropyl methylcellulose powder are mixed and stirred to form a gel. The viscous gel thus formed can improve the adhesion of the graft material powder. For example, the stirring may be performed using a mixer. As the graft material powder is stirred with the hydroxypropyl methylcellulose in powder form, a product with homogeneous quality can be obtained.

According to one embodiment of the present disclosure, the volume ratio between the graft material powder having the bone morphogenetic protein adsorbed thereon and the hydroxypropyl methylcellulose powder may be 1:0.2 to 1:0.6. If the volume ratio of the hydroxypropyl methylcellulose powder is less than 0.2, it may be difficult to form a gel, and if the volume ratio of the hydroxypropyl methylcellulose powder is more than 0.6, it may be difficult to form an effective bone graft composition because the volume of the gel is larger than the volume of the graft material powder. In terms of the effects of the present disclosure, the volume ratio between the graft material powder having the bone morphogenetic protein adsorbed and thereon the hydroxypropyl methylcellulose powder may preferably be 1:0.25 to 1:0.35.

Thereafter, the mixture of the graft material powder and the hydroxypropyl methylcellulose powder, obtained by the mixing and stirring process, is freeze-dried under vacuum to form a sponge-like structure containing pores. A sponge-like structure containing a plurality of pores may also be formed by freeze-drying the mixture of the graft material powder and the hydroxypropyl methylcellulose powder, obtained by the mixing and stirring process, at a low temperature under vacuum.

A sponge-like structure including a porous structure may be formed by the freeze-drying treatment under vacuum. The gel may be absorbed into the graft material powder to form a sponge-like structure including a porous structure, and it is believed that the treatment under vacuum mainly contributes to the formation of the sponge-like structure including a porous structure.

According to one embodiment 41 of the present disclosure, the method for preparing the bone graft composition may further include a packaging step.

According to one embodiment of the present disclosure, the method for preparing the bone graft composition may further include a step of placing the prepared bone graft composition including a sponge-like structure containing a plurality of pores in a snap tube sized to be inserted into a syringe. When the method further includes the step of placing the composition in a snap tube sized to be inserted into a syringe, the composition may be sized to be inserted into the syringe and thus may be inserted directly into the syringe without a separate process, so that the operation of the process be for preparing the bone graft composition can b facilitated.

According to an embodiment of the present disclosure, the method for preparing the bone graft composition may further include a step of placing and sealing the bone graft composition including a sponge-like structure containing a plurality of pores, placed in the snap tube, in a syringe. When the bone graft composition is provided in the syringe, it is possible to ensure ease of use and significantly reduce the possibility of contamination that may occur during use.

According to one embodiment of the present disclosure, the method for preparing the bone graft composition may further include a step of sterilizing the composition.

In one embodiment of the present disclosure, the bone graft composition including a sponge-like structure containing a plurality of pores may be sterilized by ethylene oxide gas. For example, the concentration of the ethylene oxide gas may be 450 to 1,200 mg/l.

If the concentration of the ethylene oxide gas is less than 450 mg/l, sterilization may be insufficient, and if the concentration of the ethylene oxide gas is more than 1,200 mg/l, denaturation of the bone morphogenetic protein may occur.

According to one embodiment of the present disclosure, the bone graft composition including a sponge-like structure containing a plurality of pores may be sterilized by gamma-ray irradiation. For example, the dose of the gamma-ray irradiation may be 10 to 25 kGy. If the dose of the gamma-ray irradiation is less than 10 kGy, sterilization may be insufficient, and if the dose of the gamma-ray irradiation is more than 25 kGy, denaturation of the bone morphogenetic protein may occur.

The bone graft composition according to the embodiment of the present disclosure, which may be prepared according to the above-described method, may have shape retainability for application of the composition to the human body, for example, application of the bone graft composition to missing teeth. This shape retainability may be determined by the content of hydroxypropyl methylcellulose (HPMC) or the like in the bone graft composition.

For example, in the case in which a bone graft material is applied to teeth, when a dental operator applies the bone graft material to a missing tooth, the bone graft material should have a predetermined degree of plasticity so that it can be deformed to fit the shape of the missing tooth. In addition, after the bone graft material is applied to the missing tooth, the phenomenon that the bone graft composition flows out around or detaches should not occur. Thus, the bone graft material should have a predetermined degree or more of plasticity, and should also have a predetermined degree or more of strength that can resist gravity or the movement of the bone (tooth) defect.

This degree of strength and plasticity may be defined as shape retainability. Shape retainability can be defined by the change rate of the short-axis that can be quantified as the spherical shape of a spherical sample having a diameter of several millimeters (mms) is deformed into an elliptical shape when a force of several newtons (Ns) is applied to the sample, in order to quantify the objective degree of shape retainability.

In order to satisfy the above-described plasticity and stiffness, the shape retainability of the bone graft composition should be 50 or more. If the shape retainability is less than 50, the bone graft composition may be difficult to apply to a bone defect, due to the strong elasticity thereof. That is, when a medical operator applies the bone graft composition to a bone defect, the bone graft composition should be deformed to fit the shape of the bone defect, but if the elasticity of the bone graft composition is strong, the bone graft composition may be difficult to deform due to the high resilience of the bone graft composition. On the other hand, if the shape retainability is less than 50, the bone graft composition may flow out around during a medical procedure such as hydration that is performed by a medical operator, and hence it is virtually impossible to perform the medical procedure.

Thus, in order to ensure the applicability of the bone graft composition while ensuring the ease of the actual medical procedure, the "maximum breaking force (N)/short-axis change rate" of the bone graft composition should be 50 or more, and in this case, the bone graft composition is easy to deform to fit the shape of the bone defect due to the excellent shape retainability thereof, and it is possible to obtain a bone graft composition that do not have problems, such as a phenomenon in which the bone graft composition flows out around during a medical procedure such as hydration which is performed by a medical operator. To this end, the content of hydroxypropyl methylcellulose is 0.3 to 3 parts by weight based on 1 part by weight of the bone graft material, and in this case, it is possible to obtain a bone graft composition having shape retainability of 50 or more.

Hereinafter, preferred examples will be presented to help the understanding of the present disclosure. However, these examples are merely to illustrate the present disclosure and are not intended to limit the scope of the present disclosure as defined in the appended claims. In addition, it will be obvious to those skilled in the art that various changes and modifications of these examples are possible without departing from the scope and technical spirit of the present disclosure. In addition, it is to be understood that these changes and modifications also fall within the appended claims.

Experimental Example 1

1. Experiment for Examining Shape Retainability Depending on Content of Hydroxypropyl Methylcellulose (HPMC)

As shown in Table 1 below, varying amounts (0.1 to 6 parts by weight) of HPMC was each mixed with 0.25 g of a bone graft material, and then dissolved in a solvent (DBS) to form viscous gels which were then shaped into spheres. The size of each initial sphere is shown as the long-axis length and the short-axis axis length in Table 1 below. A pressing force was applied to each of the spheres using a push-pull gage, and the short-axis length at the maximum breaking force (N) immediately before each sphere was broken, that is, the maximum peak value, was measured. The short-axis change rate obtained by comparing the short-axis length at the maximum breaking force with the initial short-axis length is shown in Table 1 below.

2. Experiment for Examining Strength Depending on Content of HPMC (Hydroxypropyl Methylcellulose)

In Experimental Example 1 above, the maximum breaking force (N) immediately before each sphere was broken, that is, the maximum peak value, was measured. The results of the measurement are shown in Table 1 below. It can be interpreted that the greater the maximum breaking force (N), the greater the strength.

TABLE 1

| Content (parts by weight) | Long-axis length (mm) | Short-axis length (mm) | Maximum breaking force (kgf) | Maximum breaking force (N) | Short-axis length (mm) after change | Short-axis change rate (%) |
| --- | --- | --- | --- | --- | --- | --- |
| 0.1 | 8.32 | 8.18 | 1.04 | 10.18 | 3.53 | 43.15 |
| 0.2 | 8.85 | 8.56 | 1.37 | 13.39 | 3.61 | 42.17 |
| 0.3 | 8.72 | 8.53 | 2.32 | 22.69 | 3.36 | 42.56 |
| 0.4 | 10.43 | 10.31 | 2.43 | 23.84 | 3.65 | 35.40 |
| 0.6 | 10.08 | 9.39 | 3.36 | 32.93 | 4.01 | 42.71 |
| 0.8 | 12.27 | 11.32 | 2.95 | 28.94 | 4.36 | 38.52 |
| 1.2 | 11.48 | 10.65 | 3.36 | 32.90 | 4.80 | 45.07 |
| 1.5 | 12.88 | 12.60 | 3.06 | 30.01 | 5.36 | 42.54 |
| 2 | 13.15 | 13.03 | 3.45 | 33.80 | 6.42 | 49.27 |
| 3 | 16.50 | 14.90 | 3.55 | 34.75 | 9.45 | 63.42 |
| 4 | 17.43 | 17.03 | 2.63 | 25.74 | 10.58 | 62.13 |
| 5 | 18.51 | 18.11 | 1.89 | 18.52 | 11.15 | 61.57 |
| 6 | 19.10 | 18.47 | 1.33 | 13.08 | 12.10 | 65.51 |

3. Examination of Shape Retainability Using Maximum Breaking Force (N) Relative to Short-Axis Change Rate In order to form a bone graft composition having excellent shape retainability, optimal strength and non-resilience are required. Table 2 below shows the maximum breaking force relative to the short-axis change rate depending on the content of HPMC (hydroxypropyl methylcellulose). FIG. 2 shows "maximum breaking force (N) of bone graft composition sphere/short-axis change rate of bone graft composition sphere" as a function of the content (parts by weight) of hydroxypropyl methylcellulose, calculated based on the results shown in Table 2.

TABLE 2

| Content (parts by weight) | Maximum breaking force (N)/ short-axis change rate |
| --- | --- |
| 0.1 | 23.6 |
| 0.2 | 31.8 |
| 0.3 | 53.3 |
| 0.4 | 67.3 |
| 0.6 | 77.1 |
| 0.8 | 75.1 |
| 1.2 | 73.0 |
| 1.5 | 70.5 |
| 2 | 68.6 |
| 3 | 54.8 |
| 4 | 41.4 |
| 5 | 30.1 |
| 6 | 20.0 |

When the content of hydroxypropyl methylcellulose (HPMC) was 0.1 to 0.2 parts by weight, the short-axis change rate was high and the maximum breaking force (N) was low. Thus, in this case, the "maximum breaking force (N)/short-axis change rate" value was low, and hence the shape retainability was not excellent. This means that the shape is easily changed even with a slight force, and this change is very unfavorable during a medical procedure for application of the bone graft composition. This is understood as a phenomenon occurring because the amount of the HPMC capable of increasing the stiffness of the bone graft composition is small.

In addition, in the case of each of the bone graft compositions containing 4 parts by weight or more of hydroxypropyl methylcellulose (HPMC), the short-axis change rate was high and the maximum breaking force (N) was low. Thus, in this case, the "maximum breaking force (N)/short-axis change rate" value was low, and hence the shape retainability was not excellent. That is, it can be seen that, when the content of HPMC in the bone graft composition is excessively high (4 parts by weight or more), the HPMC decreases the shape retainability of the bone graft composition without increasing the stiffness of the bone graft composition.

When hydroxypropyl methylcellulose (HPMC) is contained in an amount of 0.3 to 3 parts by weight based on 1 part by weight of the bone graft material, it is possible to obtain a bone graft composition having excellent shape retainability due to a "maximum breaking force (N)/short-axis change rate" of 50 or more. In another example, when hydroxypropyl methylcellulose (HPMC) is contained in an amount of 0.4 to 2 parts by weight based on 1 part by weight of the bone graft material, it is possible to obtain a bone graft composition having excellent shape retainability due to a "maximum breaking force (N)/short-axis change rate" of 60 or more. In still another example, when hydroxypropyl methylcellulose (HPMC) is contained in an amount of 0.6 to 1.5 parts by weight based on 1 part by weight of the bone graft material, it is possible to obtain a bone graft composition having excellent shape retainability due to a "maximum breaking force (N)/short-axis change rate" of 70 or more.

As described above, the bone graft composition containing hydroxypropyl methylcellulose according to the present disclosure has excellent shape retainability due to the strong strength and non-resilience thereof, and has excellent effects in terms of activation of bone formation, biocompatibility, and ease of use.

What is claimed is:

1. A bone graft composition consisting of a bone graft material and hydroxypropyl methylcellulose (HPMC),
    wherein the HPMC maintains the shape of the bone graft composition after implantation in a bone defect portion so as to have a shape retainability of 50 or more,
    wherein the shape retainability is defined as a value obtained by dividing a maximum breaking force (Nmax) by a short-axis change rate, in which the maximum breaking force (Nmax) is a force at which a change in shape of a sphere-shaped material is initiated by applying a force (N) to one side of the sphere-shaped material, and the short-axis change rate is a ratio (D-S)/(D) of a reduction in short-axis length (S) of the sphere-shaped material, measured after the change in the shape occurred, to a diameter (D) of the sphere-shaped material,
    wherein the bone graft composition consists of 1 to 3 parts by weight of the HPMC with respect to 1 part by weight of the bone graft material for enhancing the shape retention ability, and
    wherein the bone graft material consists of an autogenous bone graft material, an allogeneic bone graft material, or a xenogenic bone graft material.

2. The bone graft composition of claim 1, wherein the bone graft material is a porous structure.

3. The bone graft composition of claim 1, wherein the autogenous bone graft material is an autogenous bone graft powder, the allogeneic bone graft material is a allogeneic bone graft powder, and the xenogenic bone graft material is an xenogenic bone graft powder.

4. The bone graft composition of claim 3, wherein the average particle diameter (D50) of the autogenous bone graft powder, the allogeneic bone graft powder, and the xenogenic bone graft powder is between 200 μm and 5,000 μm.

5. The bone graft composition of claim 4, wherein the average particle diameter (D50) of the autogenous bone graft powder, the allogeneic bone graft powder, and the xenogenic bone graft powder is between 250 μm and 1,000 μm.

6. A bone graft composition comprising a bone graft material and hydroxypropyl methylcellulose (HPMC),
    wherein the HPMC maintains the shape of the bone graft composition after implantation in a bone defect portion so as to have a shape retainability of 50 or more,
    wherein the shape retainability is defined as a value obtained by dividing a maximum breaking force (Nmax) by a short-axis change rate, in which the maximum breaking force (Nmax) is a force at which a change in shape of a sphere-shaped material is initiated by applying a force (N) to one side of the sphere-shaped material, and the short-axis change rate is a ratio (D-S)/(D) of a reduction in short-axis length(S) of the sphere-shaped material, measured after the change in the shape occurred, to a diameter (D) of the sphere-shaped material,
    wherein the bone graft composition comprises of 0.3 to 3 parts by weight of the HPMC with respect to 1 part by weight of the bone graft material for enhancing the shape retention ability,
    wherein the bone graft material consists of an autogenous bone graft powder, an allogeneic bone graft powder, or a xenogenic bone graft powder and a bone morphogenetic protein adsorbed thereon, and
    wherein the HPMC is a HPMC powder.

7. The bone graft composition of claim 6, wherein the bone graft composition comprises 0.4 to 2 parts by weight of the HPMC with respect to 1 part by weight of the bone graft material.

8. The bone graft composition of claim 7, wherein the bone graft material comprises a porous structure.

9. The bone graft composition of claim 6, wherein the bone graft composition has a maximum breaking force in the range of 10 N to 35 N.

10. The bone graft composition of claim 6, wherein the bone graft composition consists of 0.3 to 3 parts by weight of the HPMC powder with respect to 1 part by weight of the bone graft material.

11. The bone graft composition of claim 6, wherein the volume ratio of the bone graft material and the HPMC powder is 1:0.2 to 1:0.6.

12. The bone graft composition of claim 10, wherein the bone graft composition consists of 0.4 to 2 parts by weight of the HPMC powder with respect to 1 part by weight of the bone graft material.

13. The bone graft composition of claim 10, wherein the bone graft composition consists of 0.6 to 1.5 parts by weight of the HPMC powder with respect to 1 part by weight of the bone graft material.

14. The bone graft composition of claim 10, wherein the bone graft composition consists of 1 to 3 parts by weight of the HPMC powder with respect to 1 part by weight of the bone graft material.

15. The bone graft composition of claim 6, wherein the average particle diameter (D50) of the autogenous bone graft powder, the allogeneic bone graft powder, and the xenogenic bone graft powder is between 200 μm and 5,000 μm.

16. The bone graft composition of claim 15, wherein the average particle diameter (D50) of the autogenous bone graft powder, the allogeneic bone graft powder, and the xenogenic bone graft powder is between 250 μm and 1,000 μm.

17. The bone graft composition of claim 6, wherein bone morphogenetic protein is rhBMP-2.

18. The bone graft composition of claim 6, wherein the bone graft composition consists of the bone graft material and the HPMC.

19. A bone graft composition comprising a bone graft material and hydroxypropyl methylcellulose (HPMC),
    wherein the HPMC maintains the shape of the bone graft composition after implantation in a bone defect portion so as to have a shape retainability of 50 or more,
    wherein the shape retainability is defined as a value obtained by dividing a maximum breaking force (Nmax) by a short-axis change rate, in which the maximum breaking force (Nmax) is a force at which a change in shape of a sphere-shaped material is initiated by applying a force (N) to one side of the sphere-shaped material, and the short-axis change rate is a ratio (D-S)/(D) of a reduction in short-axis length(S) of the sphere-shaped material, measured after the change in the shape occurred, to a diameter (D) of the sphere-shaped material, wherein the bone graft composition comprises 0.6 to 1.5 parts by weight of the HPMC with respect to 1 part by weight of the bone graft material for enhancing the shape retention ability, wherein the bone graft material consists of an autogenous bone graft powder, an allogeneic bone graft powder, or a xenogenic bone graft powder and a bone morphogenetic protein adsorbed thereon, and wherein the HPMC is a HPMC powder.

20. The bone graft composition of claim 19, wherein the bone graft material comprises a porous structure.

* * * * *